United States Patent [19]

Kask et al.

[11] Patent Number: 5,137,712
[45] Date of Patent: Aug. 11, 1992

[54] USE OF S-ADENOSYL-L-METHIONINE (SAME) TO REVERSE AND/OR PREVENT SUPERSENSITIVITY, TOLERANCE AND EXTRAPYRAMIDAL SIDE EFFECTS INDUCED BY NEUROLEPTIC TREATMENT

[75] Inventors: Anne M. Kask, Bakerton, W. Va.; Concepcio Marin, Bethesda, Md.

[73] Assignee: The United States of America as represented by the Secretary of the Department of Health and Human Services, Washington, D.C.

[21] Appl. No.: 575,808

[22] Filed: Aug. 31, 1990

[51] Int. Cl.⁵ .................... A61K 49/00; A61K 31/54; A01N 43/04
[52] U.S. Cl. ...................... 424/10; 514/46; 514/922; 514/224.8
[58] Field of Search ............. 514/970, 46, 922, 224.8, 514/437, 217, 277; 424/10

[56] References Cited

U.S. PATENT DOCUMENTS 4,369,177 1/1983 Kozaki .............................. 424/175

OTHER PUBLICATIONS

Dorris "Effects of . . . " J. Dental Research 69:148, Abst. #313, Mar. 1990.
Goodman *The Pharmacological Bases of Therapeutics*, pp. 405–407 (1985).
*Merck Manual*, p. 2488.
Kask Marin, 3'Chase "S-Adenosyl-L-Methionine . . . " Soc. Nurosci Abstr. 15(1): 268 (1989).
Costall et al., (1973) Arzneim.-Forsch. (Drug Res.) 5:674-683.
Janssen et al., (1965) Arzneim.-Forsch. (Drug Res.), 15:104- 17
Seeman et al., (1976), Nature, 6:717-719.
Rupniak et al., (1983) Life Sciences 32:2289-2311.
Creese et al., (1976) Science 192:481-483.
S. Snyder, (1988) Neuropsychopharmacology, 11:197-199.
A. Carlsson, (1988) Neuropsychopharmacology, 1:179-186.
Richelson et al., (1984), European Journal of Pharmacology, 103:197-204.
D. Pickar, (1988), Schizophrenia Bulletin 14(2):255-267.
Oates et al., (1991) The New England Journal of Medicine, vol. 324, No. 11:746-754.
Crews et al., (1983) Psychopharmacology 81:208-213.
Crews (1982) Psychopharmacology Bulletin 18:135-143.
Hirata et al. (1979) Cell Biology 76:368-372.
Owen et al. (1980) Life Sciences 26:55-59.
Baldessarini, M.D. (1987) The American Journal of Medicine 83 (Suppl. 5A):95-103.
Gerlach et al. (1988) Acta Psychiatr. Scand. 77:369-378.
Devanand et al. (1989) Arch. Neurol. 46:854-857.
Steardo et al. (1985) Journal of Neurochemistry 45:784-790.
Loesberg et al. (1989) Life Sciences 45:1227-1235.
Sakamoto et al. (1989) Eur. J. Immunol. 19:873-879.
Briley et al. (1978) European Journal of Pharmacology 50:283-284.

(List continued on next page.)

*Primary Examiner*—Frederick E. Waddell
*Assistant Examiner*—Gregory Hook
*Attorney, Agent, or Firm*—Birch, Stewart, Kolasch and Birch

[57] ABSTRACT

A method for reversing or preventing the onset of tolerance and the development of extrapyramidal side effects in humans due to prolonged treatment with neuroleptics, comprising including S-adenosyl-L-methionine (SAMe) in the treatment regime. By utilizing SAMe in combination with tolerance-inducing neurolepitcs to maintain a minimum dosage of the drug while retaining its efficacy, the potential for the development of neuroleptic-induced, extrapyramidal side effects is minimized.

13 Claims, 1 Drawing Sheet

OTHER PUBLICATIONS

Parashos et al. (1989) Neurosciences Letter 105.
Le Fur et al. (1983) Life Sciences 32:2321-2328.
Hirata et al. (1980) Science 209:1082-1090.
Bhargava (1984) Neuropharmacology 23:439-444.
Cohen et al. (1988) J. Clin. Psychopharmacol. 8:43-47.
Kleinman et al. (1988) Schizophrenia Bulletin 14:209-216.
Cimino et al. (1984) Life Sciences 34:2029-2039.
Sarda et al. (1989) Dev. Pharmacol Ther. 13:104-112.
Seeman (1988) Journal of Clinical Psychopharmacology, vol. 8, No. 4, pp. 3S-9S.
Hershkowitz et al. (1982) in Progress Brian Research, Gispen et al., eds., 56:419-434.
Carney (1986) Clinical Neuropharmacology 9:235-243.
Lieberman et al. (1988) Journal of Clinical Psychopharmacology.

* Denotes significance compared to day 1 of treatment ($p<0.01$, Dunn's multiple comparisons).

USE OF S-ADENOSYL-L-METHIONINE (SAME) TO REVERSE AND/OR PREVENT SUPERSENSITIVITY, TOLERANCE AND EXTRAPYRAMIDAL SIDE EFFECTS INDUCED BY NEUROLEPTIC TREATMENT

BACKGROUND OF THE INVENTION

1. Field of the Invention

The present invention relates to a method for reversing or preventing extrapyramidal side effects consequent to neuroleptic treatment of psychiatric disorders by concurrently administering S-adenosyl-L-methionine (SAMe).

More specifically, the present invention relates to a method for reversing or preventing the onset of tolerance, and normalizing receptor binding, in patients undergoing prolonged neuroleptic treatment. Such patients often require increases in dosage to maintain therapeutic effects. Prolonged treatment also induces a proliferation of receptors, which is thought to contribute to extrapyramidal side effects often observed during treatment with neuroleptics. As a consequence of its effectiveness in reversing and/or preventing the onset of tolerance, and in normalizing receptor binding in patients undergoing treatment with neuroleptics, SAMe should find wide utility in human therapy.

2. Description of Related Art

Neuroleptic drug treatment is used in a wide variety of dementias. Chronic neuroleptic treatment with specific receptor antagonists, which occupy membrane receptors, normally up-regulates the specific receptors. Some antagonists also induce tolerance in which the dosage of drug must be increased to maintain its effect.

In contrast, supersensitivity occurs when there is an increase in bindable receptor number consequent to chronic receptor blockade with antagonist. An exaggerated response then occurs when this proliferation of binding sites is challenged with specific receptor agonist.

No drugs are presently available which are effective in preventing or reversing tolerance or normalizing receptor binding in patients undergoing prolonged neuroleptic treatment.

In many cases, the induction of tolerance and receptor proliferation supersensitivity are accompanied by undesirable extrapyramidal side effects such as tardive dyskinesia (TD). Extrapyramidal side effects are manifested as disorders in motor activities, affecting and impairing voluntary motion associated with postural, static, supporting, and locomotor mechanisms. Symptoms include tremors, muscular rigidity, dyskinesias such as TD, parkinsonism, or phenothiazene intoxication, etc. In the case of TD, specific manifestations include uncontrollable oral/facial movements such as grimacing and tongue protrusion. At present, such side effects are best prevented by using minimal dosages of neuroleptics for minimal time periods (Gerlach et al. (1988) *Acta Psychiatr. Scand* 77:369-378). The neuroleptics in use today have antidopaminergic activity, which may contribute to the development of these side effects.

As discussed by Gerlach et al., the etiology of extrapyramidal side effects, specifically TD, is not definitely known at the present time. Certain factors seem to predispose toward the development of TD, which is considered to be the most serious side effect of neuroleptic treatment. The most important predisposing factors are: treatment with neuroleptic drugs, age, psychiatric diagnosis, prior extrapyramidal syndromes, and unknown individual factors. The prevention and treatment of TD are comprehensively discussed in this review.

In Europe, S-adenosyl-L-methionine has been used without side effects to treat patients for depression. The mechanism through which SAMe acts affects many different receptor systems, as well as other non-receptor related systems. A direct correlation has been found between membrane fluidity and receptor number (e.g., beta-adrenergic receptors, Hirata et al. (1979) *Proc. Natl. Acad. Sci. USA* 76:368-72). A decrease in membrane microviscosity yields a decreased number of available receptor-type binding sites, and an increase in microviscosity yields an increased number of available binding sites. S-adenosyl-L-methionine, an endogenous compound, has been shown to affect membrane fluidity (Cohen et al. (1988) *J. Clin. Psychopharmacol.* 8:43-47), perhaps by activating the methyltransferase complex for which it serves as the methyl donor for lipid methylation (Crews (1982) *Psychopharmacol. Bull.* 18:135-43; Hirata et al. (1980) *Science* 209:1082-90; Le Fur et al. (1983) *Life Sci.* 32:2321-28).

A large proportion of presently used neuroleptics are lipid-soluble compounds, and have an affinity for the lipid core of cell membranes, to which they segregate. The presence of a neuroleptic in cell membranes can change the physical/chemical properties of cell membranes, thus changing the way receptors and other biological systems respond to their particular signals.

While SAMe has been used therapeutically as an antidepressant and an anti-inflammatory agent, its use in the presently claimed manner for treating patients undergoing neuroleptic treatment has yet to be reported.

SUMMARY OF THE INVENTION

As discovered and disclosed herein by the present inventors, the concurrent administration of SAMe or a physiologically acceptable salt thereof and neuroleptics appears to maintain a normalized membrane lipid environment, thereby preventing the tolerance and dopamine receptor upregulation usually accompanying such treatment. SAMe can be used in combination with tolerance-inducing neuroleptics such as phenothiazenes, thioxanthines, dibenzazepines, benzamides, and butyrophenones to maintain a minimum dosage of the drug while retaining the efficacy of the latter, thereby minimizing the potential for development of neuroleptic-induced extrapyramidal side effects.

Many other receptor systems have also been linked to the membrane lipid environment, and SAMe, as a direct modifier of this environment, can affect these systems. The major utility of S-adenosyl-L-methionine is as a membrane fluidizer to counteract the extrapyramidal side effects of neuroleptics, which alter membrane fluidity.

SAMe also has other possible non-neurologic uses as well. As shown by Crewes et al. (1983) *Psychopharmacology* 81:208-13, membrane microviscosity increases in rats chronically dependent on ethanol. It is therefore possible that alcohol withdrawal symptoms can be attenuated via SAMe treatment.

Similarly, SAMe can also be used to attenuate the adverse symptoms associated with detoxification due to, or withdrawal from, anticholinergics, phencyclidines, and cannabinoids.

As disclosed by Loesberg et al. (1989) *Life Sci.* 45:227-35, a relationship exists between membrane microviscosity and asthma symptoms. Experimental groups with maximal membrane fluidity showed the greatest tracheal relaxation on beta-adrenergic stimulation. As a membrane fluidizer, SAMe could therefore find possible application in the treatment of atopic or antigen-induced asthma.

Accordingly, it is an object of the present invention to provide a method for reversing or preventing extrapyramidal side effects in a human due to neuroleptic treatment, comprising concurrently administering to said human said neuroleptic and an effective anti-extrapyramidal side effect amount of S-adenosyl-L-methionine or a physiologically acceptable salt thereof.

A further object of the present invention to provide a method for attenuating alcohol withdrawal symptoms in a human, comprising administering to said human an effective alcohol withdrawal symptoms attenuating amount of S-adenosyl-L-methionine or a physiologically acceptable salt thereof.

Yet a further object of the present invention is to provide a method for treating atopic or antigen-induced asthma in a human, comprising administering to said human an effective anti-atopic or antigen-induced asthma amount of S-adenosyl-L-methionine or a physiologically acceptable salt thereof.

Another object of the present invention is to provide a method for attenuating the adverse symptoms associated with detoxification or withdrawal from anticholinergics, phencyclidines, and cannabinoids.

These objects and others are accomplished in accordance with the present invention by administering an effective antiextrapyramidal side effect amount, an effective alcohol withdrawal symptoms attenuating amount, an effective antiatopic ,or antigen-induced asthma amount, or an effective anticholinergic, phencyclidine, or cannabinoid detoxification or withdrawal symptoms attenuating amount of S-adenosyl-L-methionine or a physiologically acceptable salt thereof such as the carbonate, bicarbonate, bromide, chloride, iodide, sulfate, or p-toluenesulfonate salt. Neuroleptics against which such SAMe salts are effective include phenothiazenes, thioxanthines, dibenzazepines, benzamides, and butyrophenones, including haloperidol.

Further scope of the applicability of the present invention will become apparent from the detailed description and drawing provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
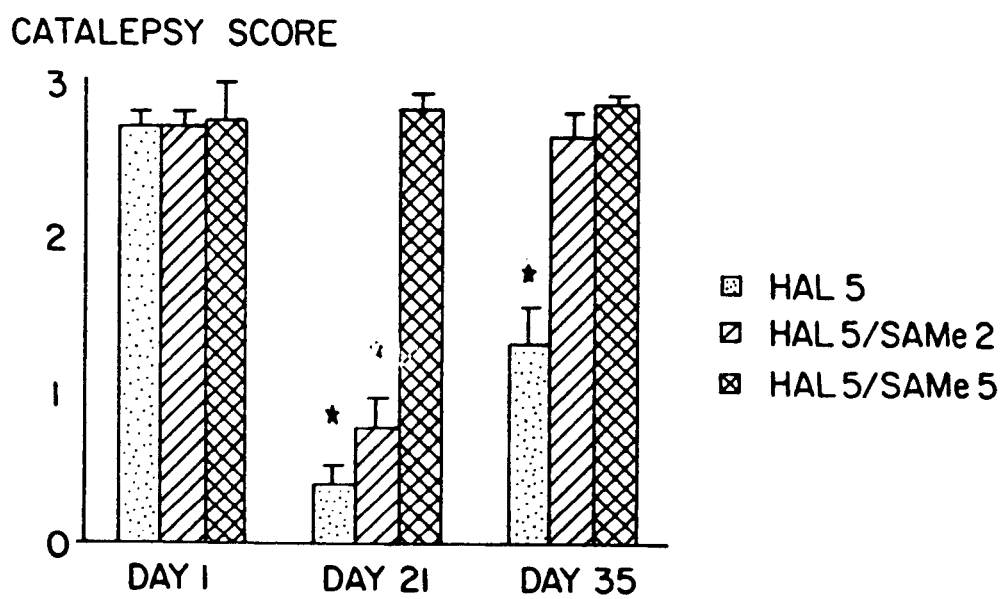
FIG. 1 shows the effect of SAMe on changes in catalepsy in rats after chronic haloperidol treatment.

The experiments described herein were designed to investigate the relationship between the dopamine (DA) receptor system and membrane microviscosity as modified by SAMe, using behavorial and biochemical methodologies to explore the effects of chronic treatments with DA D1 and D2 antagonists. The results obtained demonstrate the feasibiity of maintaining neuroleptic efficacy without the development of extrapyramidal side effects via the use of SAMe to attenuate the deleterious action of receptor antagonists.

Treatment Protocols and Membrane Analysis: Male Sprague-Dawley rats (180-200 g, 8 rats/group) were injected daily according to their treatment group. Haloperidol (HAL, a commonly employed antipsychotic agent) dosage was 1 mg/kg body weight per day (sc); SCH23390 (a benzazepine D1 antagonist), 0.1 mg/kg/day (sc), was administered in two injections of a half dose each. SAMe-p-toluenesulfonate (Sigma) was given at 50 mg/kg/day (ip). Total treatment time was five weeks. A washout period of three days was added at the end of the five week treatment period to reduce the neuroleptic concentrations in brain tissue. The eight treatment groups were: SAL-saline only; HAL only; HAL 5 weeks, SAMe final 2 weeks (HAL5/SAMe2); HAL 5 weeks, SAMe 5 weeks (HAL5/SAMe5); SCH23390 only; SCH 5 weeks, SAMe final 2 weeks (SCH5/SAMe2); SCH5 weeks, SAMe 5 weeks (SCH5/SAMe5); SAMe only. Animals were sacrificed following the washout period, the brains removed, and the striata dissected out. P2 membrane fractions were prepared from striata of pooled groups, with minor modifications, and assayed for protein content (Steardo et al. (1985) *Jour. Neurochem.* 45(3):784-90).

Receptor Binding Assay: DA D1 binding was defined by 125-I-SCH23982 (NEN,2200Ci/mmol) with cold SCH23390 as the displacer at 0.01 mM. D2 binding was assessed using 125-I-Sulpride (Amersham, 2000Ci/mmol) as the hot ligand and 0.01 mM sulpiride (Sigma) to determine non-specific binding. A saturation curve was run for each pooled group using a concentration range of 0.4-20.0 nM ligand. The assays were run in 96-well covered tissue culture plates (Costar) in a total volume of 0.3 ml/well and at a protein concentration of 0.1 mg/well for D1 and 0.15 mg/well for D2 binding. The assays were incubated at room temperature, 30 minutes for D1 and 45 minutes for D2 binding. After incubation, the well contents were transferred to a Minifold I (Schleicher & Schuell) filtration manifold for harvesting and washing the membranes. Each data point was run in triplicate, and the results counted in a Packard Multi-Prias 4 Gamma counter.

Evaluation of Drug-Induced Catalepsy: Catalepsy ratings were performed on days one, 21 and 35, the last treatment day, using the treatment drug as challenge. Two tests for catalepsy were used: the vertical grid and the horizontal bar, as described by Parashos et al. (1989). *Neurosci. Lett.* 105:169-73. In the first, rats were placed on a wire grid inclined 60° to the horizontal plane with their limbs in abduction-extension. In the horizontal bar test, the front limbs were gently placed on a horizontal bar at a level 10 cm above the cage floor. The time elapsing before the rat changed its position was recorded and scored as 0(0-14 s), 1(15-29 s), 2(30-59 s) and 3(60 or more s). All experiments began at 14.00 h in a quiet room. Catalepsy was recorded every 20 min., starting 10 min after drug administration, for a total of 150 min. At the end of the experiment, mean scores were calculated for each animal.

Effect of SAMe on Catalepsy After Chronic Haloperidol Treatment. Catalepsy, i.e., diminished responsiveness, is a measure of neuroleptic effectivenss. As shown in FIG. 1, the three treatment groups all exhibited nearly equal catalepsy scores on day 1, indicating equal effectiveness of haloperidol at this time. On day 21, the catalepsy scores for the HAL5 and HAL5-

/SAMe2 groups were significantly diminshed, while that for the HAL5/SAMe5 group which had received SAMe concurrently with HAL throughout the three week period was essentially unaffected. It should be noted that at day 21, the HAL5/SAMe2 group had not yet begun to receive SAMe treatment. On day 35, the catalepsy score for the HAL5 group remained significantly depressed as compared to that at day 1, indicating the development of tolerance to the neuroleptic. At the same time, the catalepsy scores for the HAL5-/SAMe2 and HAL5/SAMe5 groups resembled those observed at day 1, demonstrating the effectiveness of SAMe in reversing or preventing the development of tolerance to the neuroleptic.

SCH-induced catalepsy was not affected by SAMe co-treatment (data not shown), and SCH alone did not induce tolerance.

Effect of SAMe on DA D1/D2 Receptor Binding After Chronic Treatment with Selective Antagonists: DA D2 binding increased almost five-fold in animals treated chronically with HAL. Both HAL-SAMe groups, however, had a decreased Bmax compared to HAL alone, being reduced by about 50% (Table 1); the decrease, however, was not sufficient to return the binding to normal levels.

back toward normal values in both the initial concurrent group (HAL5/SAMe5) and in the delayed concurrent group (HAL5/SAMe2). Although SCH-induced catalepsy was apparently unaffected by the presence of SAMe, D1 receptor binding in the SCH-SAMe groups was not elevated as in SCH alone, nor was the Kd significantly different from normal. As shown in previous reports (Crews et al. (1982) *Psychopharmacol. Bull.* 18:135–43; Hirata et al. (1979) *Proc. Natl. Acad. Sci. USA* 76:368–72; (1980) *Science* 209:1082–90), decreases in membrane fluidity are accompanied by increases in receptor availability, and vice versa, possibly through extrusion of sequestered receptors from rigidified membranes (Hirata et al. (1980)). Fluidizing membranes allows lateral movement of the receptor proteins, and the protein chains are able to fold back into the membrane in a more normal configuration (Hirata et al. (1980); Cohen et al. (1988) *J. Clin. Psychopharmacol.* 8:43–47), sequestering the binding sites. The D1 receptors appear to behave in this manner. The opposite appears to be the case for the D2 receptors: increasing membrane fluidity increases the Bmax as shown by the increased binding in the SAMe only group. Chronic treatment with HAL also increases Bmax for D2 receptors, yet the combination of these two drugs maintains a normal cataleptic

TABLE 1

Effect of SAME on DA D1/D2 Receptor Binding After Chronic Treatment with Selective Antagonists

| | D-1 | | D-2 | |
|---|---|---|---|---|
| | Bmax | Kd | Bmax | Kd |
| Control | 586 ± 9 | 1.0 ± 0.4 | 573 ± 13 | 0.8 ± 0.2 |
| Haloperidol | 518 ± 38 | 3.3 ± 0.05 (a) | 2600 ± 21 (a) | 4.1 ± 1.1 (a) |
| HAL ± SAMe (2) | | | 1075 ± 340 (ab) | 3.9 ± 1.6 (a) |
| HAL ± SAMe (5) | 558 ± 46 | 6.6 ± 2.0 | 1040 ± 30 (ab) | 2.6 ± 0.5 (cb) |
| SCH23390 | 882 ± 76 (a) | 4.1 ± 1.2 (a) | 462 ± 50 | 1.5 ± 0.2 |
| SCH ± SAMe (2) | 513 ± 29 (b) | 1.3 ± 0.1 (b) | 457 ± 19 | 1.4 ± 0.1 |
| SCH ± SAMe (5) | 527 ± 68 (b) | 1.2 ± 0.1 (b) | 510 ± 28 | 1.2 ± 0.1 |
| SAMe | 482 ± 61 (cb) | 4.3 ± 0.2 (a) | 1720 ± 30 (ab) | 3.0 ± 1.0 (ab) |

Bmax = fmol·mg protein ± SE of the mean
Kd = nM ± SE of the mean
a = 3 (number of determinations averaged)

In the HAL group, the Kd was also elevated, possibly due to competition for high affinity binding sites by residual neuroleptic (Owen et al. (1980) *Life Sciences* 26:55–59). SAMe alone also increased the level of D2 binding and the Kd (p<0.01,Table 1), but not to the same extent as HAL alone. D1 binding in the SCH alone group was increased significantly (p<0.01) over normal values, but decreased in the SAMe alone group (p<0.05) compared to control. The Bmax and Kd values for D1 binding in both SCH+SAMe groups were not statistically different from control values, and were substantially reduced from SCH alone (p<0.01, Table 1).

These results demonstrate that the effect of SAMe on the dopaminergic receptor system appears to be a normalization of receptor activity of both the D1 and D2 receptor subtypes. Under the same treatment conditions, binding by both subtypes was altered from the usual response to chronic antagonist treatment to attenuation toward normal values. The difference in response of the receptor subtypes to SAMe was that the available D1 receptor sites decreased with chronic SAMe, while the number of D2 sites increased, with a decrease in affinity exhibited by both subtypes.

Concurrent treatment with HAL-SAMe had profound effects on HAL-induced catalepsy and D2 receptor upregulation. In the presence of SAMe, D2-mediated supersensitivity and tolerance were shifted response and lowers the Bmax value. One conclusion which can be drawn from these data is that in the case of the D2 receptors, haloperidol and SAMe do not share a common mechanism of action; however, their combined effect serves to normalize D2-mediated functional activity, perhaps with a contribution from stabilization of D1 receptor activity. HAL may exert its effect by increasing membrane microviscosity, thereby extruding sequestered or masked binding sites, and SAMe, by fluidizing membranes, may increase receptor turnover, giving rise to a situation where the net effect appears to be an attenuation of the individual effects, resulting in preservation of neuroleptic efficacy as measured by catalepsy induction. Another possible mechanism may involve the HAL high and low affinity D2 receptor subtypes (Briley et al. (1978) *Eur. J. Pharmacol.* 50:283-4) and their stereochemistry, where methylation of either membrane lipids or receptor proteins maintains a normal ratio of high/low affinity HAL-induced D2 type receptors.

The functional interaction of the DA D1 and D2 receptor subtypes as measured by behavioral and biochemical parameters does not appear to be compromised by concurrent antagonist/SAMe treatment, minimizing the possibility of undesirable side effects caused by alterations to part of a functionally linked system.

The implications for therapeutic usage can be far-reaching, not only for SAMe, but for other membrane altering drugs as well. The possibility also exists that since SAMe acts as the methyl donor for a large variety of physiological systems, one example being DNA methylation, which is important in regulation of gene expression (Sakamoto et al. (1989) *Eur. J. Immunol* 19:873-79), alterations in methylation in these other systems could affect receptor status, producing the observed results.

Pharmaceutical Preparations Containing SAMe. S-adenosyl-L-methionine, or physiologically acceptable salts thereof such as the carbonate, bicarbonate, bromide, chloride, iodide, sulfate, or p-toluenesulfonate, for example, can be formulated into a pharmaceutical composition comprising an effective anti-extrapyramidal side effect amount of the compound and a pharmaceutically acceptable carrier. An effective antiextrapyramidal side effect amount of the pharmaceutical composition will be administered to the human subject in a manner which reverses or inhibits the development of extrapyramidal side effects. The amount of the compound and the specific pharmaceutically acceptable carrier will vary depending upon the subject and his or her condition, the mode of administration, and the type of extrapyramidal side effect(s) being treated.

SAMe is administered "concurrently" with the drug which causes the extrapyramidal side effects. "Concurrent" administration denotes that SAMe is administered to the subject at a time such that SAMe will be present in the subject's system at the same time that the extrapyramidal effects would normally be observed. Thus, SAMe may be administered shortly before the neuroleptic drug, at exactly the same time as the drug, or shortly after the drug which causes extrapyramidal effects.

In a particular aspect, the pharmaceutical composition comprises a physiologically acceptable salt of SAMe effective in inhibiting or reversing the extrapyramidal side effects of neuroleptics, in effective unit dosage form. As used herein, the term "effective unit dosage" or "effective unit dose" is denoted to mean a predetermined anti-extrapyramidal side effect amount sufficient to inhibit or reverse the extrapyramidal side effects of neuroleptics in vivo. Pharmaceutically acceptable carriers are materials useful for the purpose of administering the medicament. They are preferably non-toxic, and may be liquid materials which are otherwise inert and medically acceptable, and which are compatible with the active ingredients. The pharmaceutical compositions may contain other active ingredients such as antimicrobial agents and other agents such as preservatives.

These pharmaceutical compositions may take the form of a solution, and may be concurrently administered parenterally. Said parenteral administration may be conducted intraperitoneally, intramuscularly, subcutaneously, intravenously, intraarticularly, intraarterially, or transdermally. They may preferably be given once a day as an i.v. injection containing 100 to 800 mg of active ingredient, either as a bolus or an infusion. They can also be concurrently administered orally at a rate of 10 to 20 mg/Kg/day divided into three doses, given at eight hour intervals. For oral administration, SAMe salts can be formulated into enteric coated tablets, gelatin capsules, timed-release formulations, or dispersed in compatible emulsions together with stabilizing and/or dispersing agents. SAMe can also be encapsulated in liposomes for oral use, and when such liposomes are engineered to fit into an aerosol droplet, SAMe or salts thereof can be delivered directly to the airways. Oral administration appears to be the optimal method of prescribing SAMe for most therapeutic purposes.

For attenuating alcohol withdrawal symptoms, treating atopic or antigen-induced asthma, and attenuating adverse symptoms associated with detoxification or withdrawal from anticholinergics, phencyclidines and cannabinoids, SAMe or physiologically acceptable salts thereof can be administered orally or parenterally, at the same dosages, in the manners described above. Such treatment is continued until the undesirable symptoms disappear. For treating atopic or antigen-induced asthma, encapsulation of SAMe or SAMe salts in aerosolized liposomes is believed to be a particularly effective mode of administration.

The compositions may contain the compound in an amount of from about 0.1% to about 99% by weight of the total composition, preferably about 1 to about 90% by weight of the total composition. For parenteral injection, the SAMe salt can be dissolved in water or saline solution.

Among the pharmaceutical compositions encompassed herein are those comprising SAMe, or a physiologically acceptable salt thereof, in combination with a neuroleptic selected from among phenothiazines, thioxanthines, dibenzazepines, butyrophenones, and benzamides, for example. Also encompassed herein are pharmaceutical kits comprising SAMe, or a physiologically acceptable salt thereof, and a neuroleptic.

The invention being thus described, it will be obvious that the same may be varied in many ways. Such variations are not to be regarded as a departure from the spirit or scope of the invention, and all such modifications as would be obvious to one skilled in the art are intended to be included within the scope of the following claims.

What is claimed:

1. A method for reversing or preventing extrapyramidal side effects in a human due to neuroleptic treatment comprising concurrently administering to said human said neuroleptic and an effective anti-extrapyramidal side effect amount of S-adenosyl-L-methionine or a physiologically acceptable salt thereof.

2. The method of claim 1, wherein said neuroleptic is selected from the group consisting of phenothiazines, thioxanthines, dibenzazepines, butyrophenones, and benzamides.

3. The method of claim 1, wherein said neuroleptic is haloperidol.

4. The method of claim 1, wherein said physiologically acceptable salt is selected from the group consisting of the carbonate, bicarbonate, bromide, chloride, iodide, sulfate, or p-toluenesulfonate salt of S-adenosyl-L-methionine.

5. The method of claim 1, wherein said S-adenosyl-L-methionine or physiologically acceptable salt thereof is concurrently administered orally or parenterally.

6. The method of claim 5, wherein said oral concurrent administration contains 10 to 20 mg/Kg/day of S-adenosyl-L-methionine or a physiologically acceptable salt thereof.

7. The method of claim 5, wherein said parenteral concurrent administration is conducted intraperitoneally, intramuscularly, subcutaneously, intravenously, intraarticularly, intraarterially or transdermally.

8. The method of claim 7, wherein said intravenous administration is accomplished via intravenous injection either as a bolus or an infusion.

9. The method of claim 8, wherein said intravenous injection contains 100 to 800 mg of S-adenosyl-L-methionine or a physiologically acceptable salt thereof.

10. The method of claim 9, wherein said physiolgically acceptable salt is S-adenosyl-L-methionine-p-toluenesulfonate.

11. The method of claim 1, wherein said concurrent administration consists of 100 to 800 mg of S-adenosyl-L-methionine-p-toluenesulfonate given via intravenous injection either as a bolus or an infusion.

12. A pharmaceutical composition, comprising a neuroleptic and S-adenosyl-L-methionine or a physiologically acceptable salt thereof.

13. The pharmaceutical composition of claim 12, wherein said neuroleptic is selected from the group consisting of phenothiazines, thioxanthines, dibenzazepines, butyrophenones, and benzamides.

* * * * *